United States Patent [19]

Polizzi et al.

[11] 4,356,400
[45] Oct. 26, 1982

[54] X-RAY APPARATUS ALIGNMENT METHOD AND DEVICE

[75] Inventors: Emanuel V. Polizzi, Hartland; David G. Lieder, Waukesha, both of Wis.

[73] Assignee: General Electric Company, Schenectady, N.Y.

[21] Appl. No.: 175,162

[22] Filed: Aug. 4, 1980

[51] Int. Cl.³ .......................................... G03B 41/16
[52] U.S. Cl. ................................ 378/138; 250/252.1; 378/205
[58] Field of Search ............................ 250/491, 252

[56] References Cited

U.S. PATENT DOCUMENTS

| | | | |
|---|---|---|---|
| 4,053,782 | 10/1977 | Grass | 250/491 |
| 4,092,544 | 5/1978 | Grim | 250/491 |
| 4,117,337 | 9/1978 | Staats | 250/491 |
| 4,167,675 | 9/1979 | Stodberg | 250/491 |

Primary Examiner—Craig E. Church
Attorney, Agent, or Firm—Wheeler, House, Fuller & Hohenfeldt

[57] ABSTRACT

In x-ray apparatus where the central ray of an x-ray beam must be made perpendicular to the planes of one or more image receptors, a central ray locator is coupled to the beam output port of an x-ray tube casing and the central ray is indicated when a luminescent spot occurs at the intersection point of cross hairs on a phosphor screen. A laser device then replaces the locator. Its beam simulates the central ray and coincides with it and provides a visual indication of it. The laser beam enables determining if the tube casing is moving in a straight vertical line by observing the movements of the laser beam light spot while it is projected on a plane surface. Procedures are disclosed for establishing the simulated central ray in perpendicularity with receptor planes.

6 Claims, 7 Drawing Figures

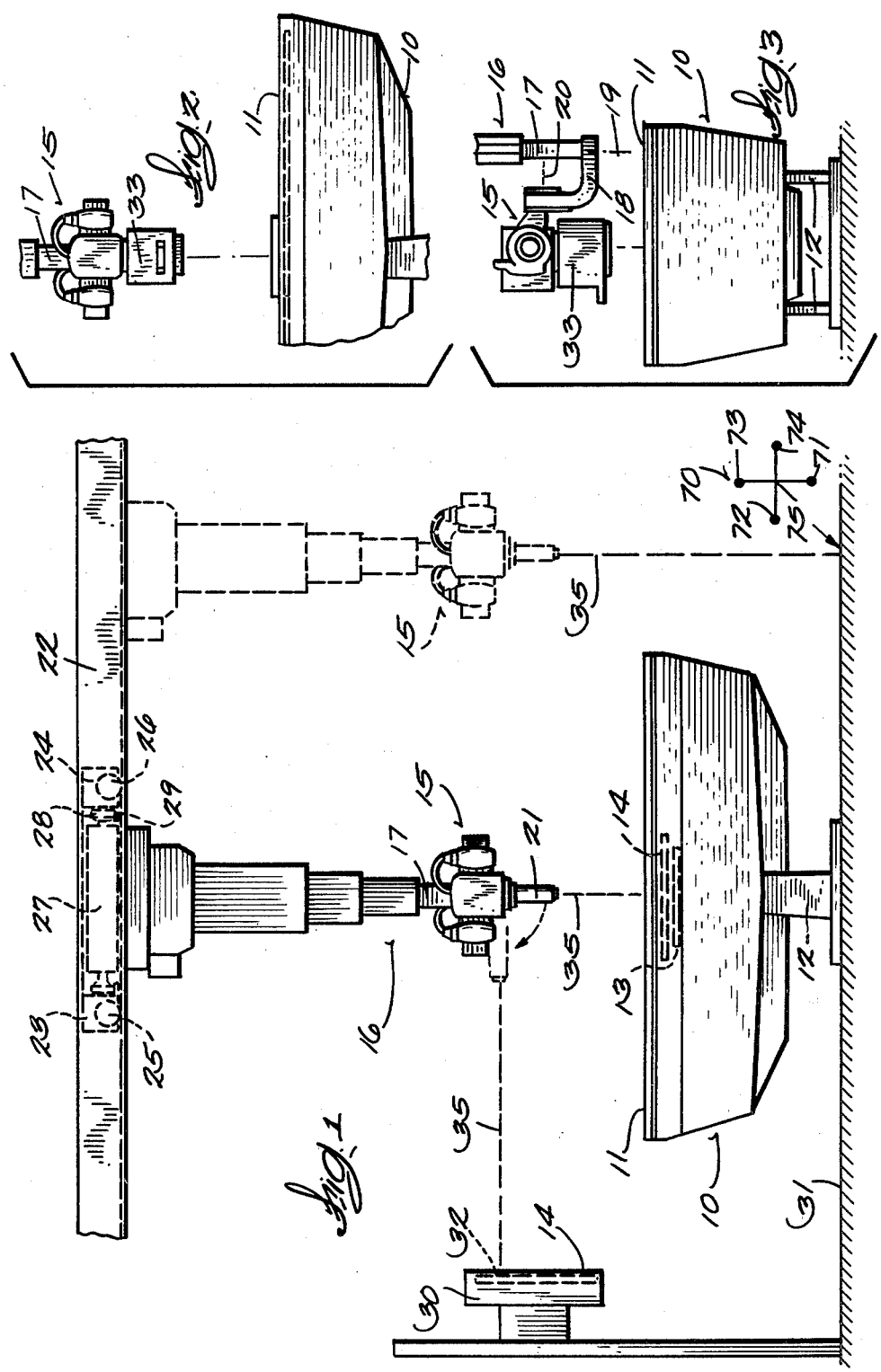

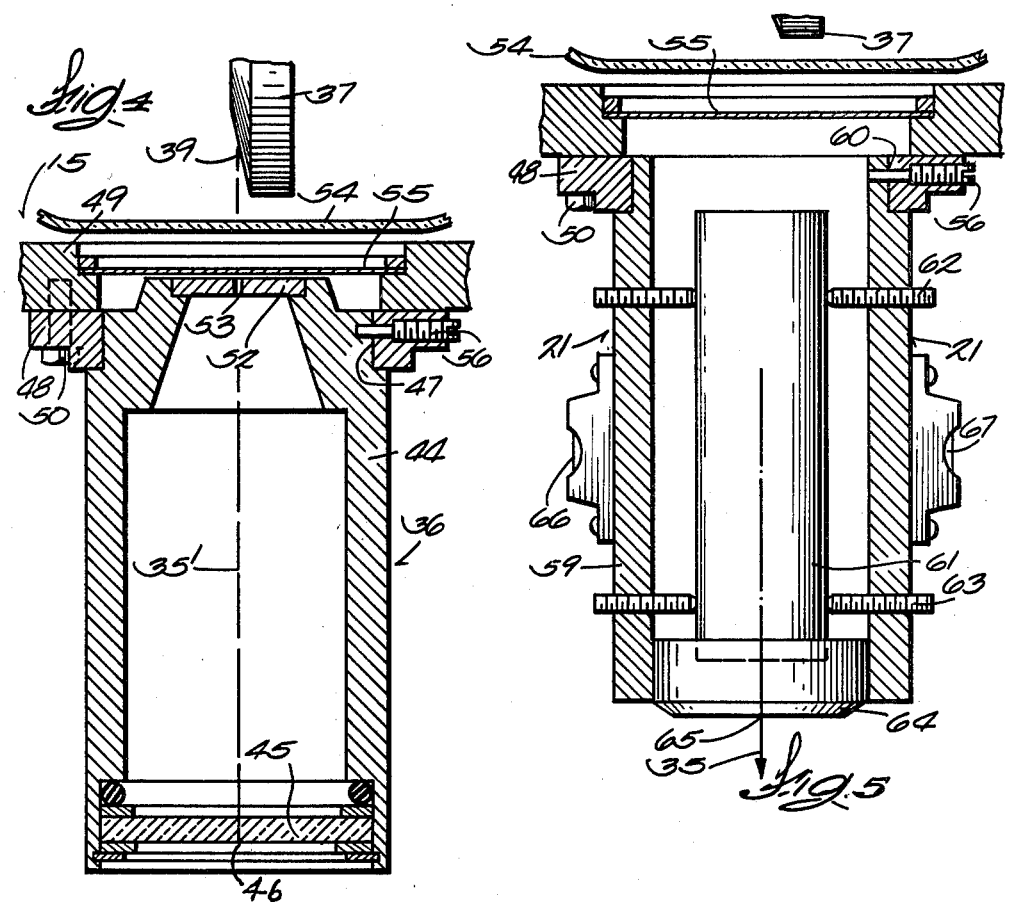
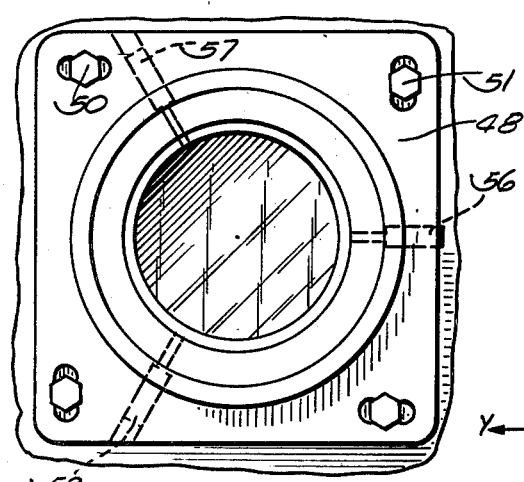
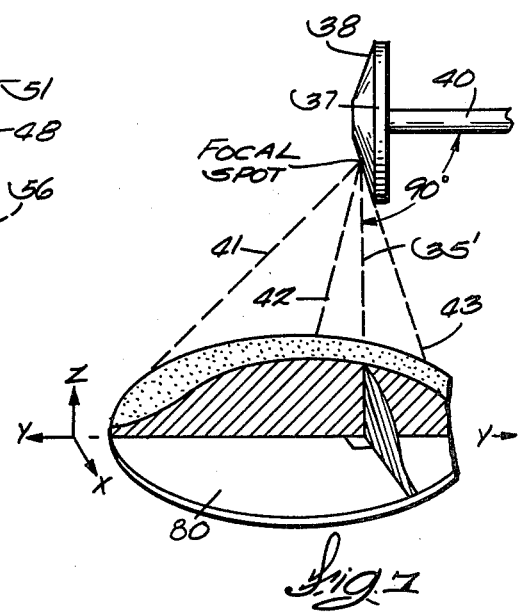

X-RAY APPARATUS ALIGNMENT METHOD AND DEVICE

This invention pertains to a method and device for aligning the central ray of a beam from an x-ray tube with one or more image receptors in a diagnostic x-ray system such that alignment is maintained even though there is relative movement between the x-ray tube and receptor.

As is well-known, if the central ray is not centered to and perpendicular to any image receptor in the system, then the x-ray field will shift laterally along the receptor plane as the x-ray tube is moved toward and away from the receptor plane.

In one type of diagnostic x-ray system, the x-ray tube is mounted on a bilaterally movable carriage having a vertical telescopic column and a swivel connection to the tube casing which enables movement of the tube and angulation of the x-ray beam in all directions. This type of system includes a patient supporting table which contains an image receptor such as a radiographic film holder or an image intensifier and a wall mounted or floor stand mounted image receptor which also contains a radiographic film holder. Before the system is put into use, it must be adjusted so that the central ray of the beam which emerges from the x-ray tube is centered and perpendicular to the receptors in the table and the wall mounted device. Centering and perpendicularlity must be maintained even when the x-ray tube or source-to-image distance (SID) is varied or when the tube angulation and, hence, beam angulation is changed from horizontal to vertical. This requirement results from the fact that a beam emerging from the x-ray tube and its central ray must be directed vertically into perpendicularity with the image receptor in the x-ray table for those procedures where the patient is supine on the x-ray tabletop and the tube must be rotated for its beam and central ray to be directed horizontally when a radiograph of a chest, for example, is to be made with the patient standing in contact with the wall or floor mounted image receptor.

One undesirable consequence of the x-ray field shifting on the receptor is that the field will extend past one edge of the receptor and fall short of the opposite edge which means that the patient will get some x-ray dosage which will not yield any diagnostic information. Moreover, it is customary to have a bucky grid superimposed over the image receptor to intercept radiation which is scattered by the body being examined. If the central ray of the x-ray beam is not perpendicular to the plane of the grid, the beam will be non-uniformly attenuated across the image receptor plane. Any shift of the x-ray field on the receptor due to necessary variations of the focal spot or source-to-image distance will cause loss of radiographic information on the edge that extends beyond the receptor.

The traditional approach to effectuating alignment of the focal spot of the x-ray tube along a line coincident with the central ray of the beam emerging from the focal spot and the plane of the receptor involves taking a series of radiographs and making any alignment adjustments required in the components of the system until the beam field was shown to stay within the margins of all the receptors in the system regardless of the position of the x-ray tube relative to the receptors. As any installer of x-ray apparatus will attest, this empirical approach to establishing central ray perpendicularity and alignment requires exposure of many expensive x-ray films before satisfactory alignment is achieved. This is so because exposures must be made with the x-ray tube set at various distances from the receptor to assure that the field does not shift when the telescopic tube supporting column is raised and lowered to the various positions in which it is intended to be used. An additional disadvantage of this repetitive film exposure procedure is that the serviceperson or installer and any one else working in the area where the apparatus is being installed may be repeatedly exposed to some scattered radiation which contributes to reaching the limits of tolerable cumulative dose.

SUMMARY OF THE INVENTION

The primary object of the present invention is to provide a device and method for aligning an x-ray source with an image receptor such that the above-mentioned problems resulting from misalignment and nonperpendicularity of the central ray may be avoided. Additional objects are to minimize the time required to properly align the components of a diagnostic x-ray system and to reduce the hazard of x-ray exposure to the installer.

In accordance with the invention, a method of determinng perpendicularity of the central ray of an x-ray beam to an image receptor plane involves mounting a cylindrical central ray locating device over the x-ray beam output port on the x-ray tube casing in a manner that allows the device to be shifted laterally by a small amount. The cylindrical device has a metal disk element in which there is a small hole that is coincident with the central axis of the cylinder. There is also a phosphor screen with cross hairs scribed on it at a fixed axial distance from the disk and the axis of the hole in the disk is perpendicular to the plane of the screen. The x-ray tube is energized to emit rays at various angles from its focal spot and the device is shifted until the bright spot on the phosphor screen coincides with the intersection of the cross hairs which is an indication that the central ray has been found. Only the ray or small ray bundle which does not enter the hole in the disk at an angle will strike the phosphor screen at the intersection of its cross hairs to produce the bright spot. The shiftable mounting plate which holds the central ray locating device to the x-ray tube casing during central ray location is then tightened or clamped in place and the device is removed from the clamped plate.

A cylinder containing a laser whose output beam is coincident with the axis of the cylinder is then secured in the mounting plate. Since the cylinder of the central ray locating device and the cylinder containing the laser are fitted into the same mounting plate and are coaxial, the laser beam becomes coincident with the line on which the central ray lies.

The laser is now mounted on the x-ray tube casing, the casing is mounted on a gooseneck, the gooseneck is mounted on a vertically telescopic column, the column is mounted on a laterally movable overhead carriage that is mounted on a longitudinally movable carriage which runs on overhead tracks. The next step in the alignment method is to lock the longitudinally and laterally movable carriages and then energize the laser so its beam is projected onto the floor with the x-ray tube casing at an intermediate elevation at about the midpoint of its upward and downward vertical travel limits. With the laser energized, a bright spot appears on the floor and a mark is made coincident with the spot. The gooseneck is then revolved about its vertical axis in 90° steps and three more light spots are marked at the intermediate level. Diametrically opposite pairs of the marks where the light spots were, are then connected by perpendicular lines for defining the tentative position of the central ray where the lines intersect. This procedure is repeated with the x-ray tube at various elevations above and below the intermediate elevation. Usually going through the procedure with the x-ray tube first at its intermediate position and then at its upper and lower limits is sufficient. Any inaccuracies in vertical travel of the x-ray tube casing on its telescopic support will be manifested by a failure of the light spots and points of diametral line intersections to coincide. The tube support, particularly the telescopic column components, are then shimmed or otherwise adjusted and the process is repeated until coincidence of the spots is obtained at all levels. It is then certain that the corresponding central ray, which is simulated by the laser beam, will be directed vertically. After all receptors have been leveled by use of a spirit level, for example, the x-ray tube casing, having the laser attached, is then shifted as required to direct the laser beam onto any one of the image receptors in the system to determine if its laser light spot falls on the center or other reference point on the receptors for those predetermined positions of the tube where the x-ray beam should be centered for making an exposure. The position of the receptor or the component which supports it is then adjusted until the laser beam spot coincides with the receptor center. A flat mirror is placed on the image receptor and the laser beam is directed at it. If the beam is reflected back along its incident path such that no reflected light spot can be seen on the body of the laser light source or if the spot is very close to the beam exit aperture, it is known that the simulated central ray and receptor plane are perpendicular. With these and other adjustments made, the laser can be removed and the regular x-ray beam collimator can be secured in the mounting plate on the tube casing and radiographs may be made with confidence that the collimator will define a field which does not overlap one edge of the receptor and fall short of the opposite edge.

A more detailed description of the x-ray system alignment method and the devices used therein will now be set forth in reference to the drawing.

DESCRIPTION OF THE DRAWING

FIG. 1 is a front elevational view of one type of diagnostic x-ray system wherein the central ray of an x-ray beam may be aligned perpendicular to one or more image receptors using the devices and method described herein;

FIG. 2 is a partial front elevational view of an x-ray table with an x-ray tube casing and an attached collimator positioned over the table;

FIG. 3 is a side elevational view of the x-ray table body and part of the x-ray tube suspension system illustrated in the preceding figures;

FIG. 4 is a longitudinal section of a central ray locating device attached to an x-ray tube casing which is shown fragmentarily;

FIG. 5 is a longitudinal section of a laser alignment device which is mounted to the tube casing;

FIG. 6 is a bottom view of the central ray locating device and its mounting plate; and FIG. 7 is a diagram for facilitating definition of central ray.

DESCRIPTION OF A PREFERRED EMBODIMENT

The illustrative x-ray system depicted in FIG. 1 comprises an x-ray table body 10 which has a patient supporting x-ray transmissive tabletop 11. The table is mounted on a stand 12 and is adapted to tilt from the horizontal position in which it is shown through opposite angular directions. An x-ray film cassette and the tray which supports it is symbolized by a dashed line rectangle 13. An x-ray grid, symbolized by the dashed line rectangle marked 14, is located over film cassette 13. This is a typical so-called bucky grid comprised of thin lead strips cast in x-ray transmissive resin with samll spaces between them so that an x-ray beam which is directed generally perpendicularly to the plane of the grid will pass through the spaces between the strips and impinge on a radiographic film in the cassette while the radiation which is scattered by a body being examined on the tabletop will be intercepted by the lead strips. The lead strips are parallel to the long axis of the x-ray tabletop. As is known, the bucky grid is customarily supported in a tray which is oscillated laterally of the tabletop, that is, crosswise of the x-ray tabletop 11 or perpendicular to the plane of the FIG. 1 drawing sheet when a radiograph is being taken so that the grids are not imaged in a fixed position on the film in the cassette 13. An x-ray tube casing 15 is supported on a vertically extensible and contractible column 16 composed of telescoping and mechanically interconnected sections. As can be seen in FIG. 3, the lowermost section 17 of the telescopic arm has an L-shaped member 18 fastened to it. This member is called a gooseneck for convenience. The gooseneck 18 is journaled for rotation about a vertical axis of the telescopic column for swinging in a horizontal plane. Tube casing 15 is also journaled on the upper end of the gooseneck for enabling it to be rotated about a horizontal axis indicated by the dashed line marked 20. In FIG. 2, a typical x-ray beam collimator 33 is shown mounted to the bottom of the x-ray tube casing 15 as would be the case when the system is being used for making radiographs whereas, in FIG. 1, the collimator has been temporarily replaced by a laser alignment tool which is generally designated by the reference numeral 21 for use in the central ray and receptor alignment procedure which will be discussed in more detail later. FIG. 2 is a front elevation of the table 10, the tube casing 15 and collimator 33.

As shown in FIG. 1, x-ray tube casing 15 is mounted for moving trilaterally, that is, vertically, longitudinally or lengthwise of tabletop 11 and transversely of the tabletop or perpendicular to the longitudinal direction. Vertical movement is obtained by extending or contracting telescopic column 16. The column 16 is indirectly mounted on longitudinally directed overhead rails, one of which, marked 22, is visible in FIG. 1. The other parallel rail, not visible, is in the same plane and behind rail 22. A bridge comprised of a pair of beams 23 and 24 which are joined together at their ends and extend transversely of the room, have wheels such as those marked 25 and 26, which permit longitudinal movement of the bridge, along rails 22. The telescopic column is mounted to a carriage or trolley 27 which also has wheels 28 for running on rails 29 to enable the carriage to move transversely of the room and x-ray tabletop.

The system in FIG. 1 has a floor or wall mounted cassette holder 30 for making chest radiographs of a patient standing on the floor 31 while the x-ray beam from the tube casing 15 is being directed through the patient and toward a cassette 32, constituting the image receptor, within cassette holder 30 instead of the beam being directed toward the bucky grid 14 and cassette 13 in the x-ray table as is the case when the patient is lying on the tabletop.

In FIG. 1, the laser alignment tool 21 is coupled to x-ray tube casing 15 as it would be when the new procedure for aligning the central ray of the x-ray beam in perpendicularity with the plane of the image receptors and with the centers of the receptors is being conducted. In FIG. 1, the fine beam of coherent radiation emitted by laser device 21 is marked 35. A laser light beam diameter of one-sixteenth of an inch has been found to be satisfactory. The alignment procedure requires locating the central ray of the x-ray beam with a locator device 36 shown in FIG. 4, and then substituting the laser device 21, shown in FIG. 5, so that the laser output beam 35 will be coincident with the central x-ray.

The term central ray as used herein is define in reference to FIG. 7. This fiure shows the x-ray tube target 37 having a beveled front fact 38 on which the focused electron beam of the tube impinges for emitting x-ray flux in all directions from a focal spot 39. Target 37 is mounted on a stem 40 which extends in the longitudinal direction from the x-ray tube rotor, not shown. The central ray is defined as the line created by the intersection of two specific planes. The first plane is that which contains the anode-cathode or stem axis of the x-ray tube and passes through the focal spot 39. The second plane also passes through the focal spot 39 but is perpendicular to the anode-cathode axis which is the same as the rotational axis of the target 37 and stem 40. The three-dimensional pattern in FIG. 7 represents the intensity and distribution of x-rays in an image receptor plane 80. The anode-cathode axis and the focal spot 39 lie in the y-z plane. As stated, the line created by the intersection of the y-x plane and the x-z plane marked 35' in FIG. 7 is the central ray. The striped planes crossing in the pattern are sections of the y-z and x-z planes. Typical boundary rays of the conical x-ray beam are marked 41, 42 and 43. The central ray does not necessarily pass through the point of maximum x-ray intensity. The location and orientation of the image receptor plane has no effect on the central ray.

The devices for locating or defining the central ray and for simulating it so it can be visualized by way of a laser beam will now be described. The central ray locator 36 is shown in FIG. 4. It comprises a hollow cylinder 44 having a phosphor screen 45 comprised of a glass substrate with a phosphor coated top surface fixed in its lower end. This screen fluoresces when it is impinged by x-radiation. The outside surface of the glass substrate has orthogonal cross hairs scribed on it. The interaction point of the cross hairs is marked 46. The upper end 47 of cylinder 44 is circular and precisely machined. The cylinder is fastened in an adapter plate 48 which has a central opening in which the reduced diameter upper end 47 of the cylinder closely fits. The adapter plate is secured to the x-ray tube casing, a fragment 49 of which is depicted in FIG. 4. Adapter plate 48 is, at the beginning of the x-ray beam central ray location process, secured loosely enough on casing 49 to permit it to be shifted or slid a small amount in any desired direction and then it is clamped tightly after the central ray is located. Adapter 48 is secured on casing 49 with four cam bolts, such as those marked 50 and 51 in FIG. 6. In the upper end of the locator device cylinder 44 there is a metal disk 52 which has a small hole 53 extending longitudinally at its center. In a commercial embodiment, by way of example, disk 52 is about 0.125 inch thick and diameter of hole 53 is 0.03 inch. The periphery of reduced diameter portion 47 of cylinder 44 is precisely concentric with the axis of hole 53. An extension of the axis of hole 53 would pass through the crosshair intersection point 46 on the screen. The hole provides a passage for the central x-ray to the phosphor screen 45. Only a ray or small ray bundle which is parallel to the hole 53 axis, that is, the central ray, will pass through the hole and strike the phosphor screen at crosshair intersection 46 where a small circular spot will be formed. When the hole is not aligned with the central ray the light spot will be offset from the point of intersection.

A portion of the glass x-ray tube envelope is marked 54 in FIG. 4. It lies immediately behind an x-ray transmissive window 55 which retains the dielectric and cooling oil within the x-ray tube casing. The window is in the x-ray beam exit port hole of the tube casing. A fragment of the x-ray tube target 37 is illustrated. The electron beam from the cathode, not illustrated, focuses on the focal spot 39 from which the x-ray flux emanates. When the central ray locator device 36 is attached as shown in FIG. 4 and the x-ray tube is energized, only the ray, as mentioned previously, which goes straight through the long hole 53, that is, the ray which is not angulated, will strike the cross hair intersection point 46. Slightly angulated rays strike the phosphor screen off the crosshair point while grossly angulated rays strike the inside surface of hole 53. Thus, when the x-ray source is turned on, no bright spot may be evident on phosphor screen 45 because the rays emanating from focal spot 39 are grossly angulated relative to the axis of hole 53 or the bright spot may be seen displaced from the crosshairs if the rays are only slightly angulated. The cylindrical locator device 36 is then shifted around laterally until the bright spot appears at the intersection point 46 of the crosshairs on screen 45. This condition indicates location of the central ray. The adaptor plate 48 is then clamped to the tube casing by tightening screws 50. The locator cylinder 36, which has heretofore been secured in adapter plate 48 by means of three set screws 56-58 is then removed from plate 48 by backing the screws out. The central x-ray is represented by the dashed line 35' in FIG. 4.

Having removed central ray locator 36 from adapter plate 48, the next step is to insert the laser alignment tool 21 of FIG. 5 into adapter plate 48. The axis of the laser tool cylindrical housing 59 is coincident with the axis of cylindrical housing 44 of the locator device 36. Thus, the laser tool comprises a hollow metal cylinder 59 and a reduced diameter portion 60 which fits into the opening in adapter plate 48 in which the locator was formerly installed. The laser device is secured in plate 48 by tightening screws 56-58. The laser tube 61 itself is secured concentrically with the interior and exterior of cylindrical housing 59 by means of two sets of radially inwardly extending screws such as the one from each set which are marked 62 and 63. Establishing the laser tube 61 and housing 59 axes in coincidence is a precision factory conducted operation but accuracy of the factory adjustment can by easily verified in the field. The focusing lens assembly for the laser tube is identified by the numeral 64. The laser beam, which preferably has a diameter of about a sixteeth of an inch emerges from the center 65 of the lens assembly. The laser beam will now be coincident with the line 35' where the central ray of the x-ray beam would exist if the x-ray tube were turned on. The laser tube housing has a pair of spirit level vials 66 and 67 mounted on it for setting the beam in a horizontal attitude as is required for some alignment operations as will be described.

After the central ray location has been determined and the laser device is in place on the x-ray tube casing 15 as it is in FIG. 1 for its beam to simulate and coincide with the central ray, the method of establishing the x-ray beam at the centers and perpendicular to the planes of the various image receptors in the system can proceed.

Assuming that the overhead carriages have been leveled and are running true, the next heretofore difficult part of the procedure involves assuring that the x-ray tube casing and, hence, the focal spot moves on a vertical line when the x-ray tube casing is being either raised or lowered by contracting or extending telescopic column 16. For this purpose, the x-ray tube is translated to a position next to the x-ray table where it is depicted in dashed lines in FIG. 1. The laser is then energized and its highly focused beam 35 is projected onto the floor 31. Because of the gooseneck 18, the beam will be offset from the vertical axis of telescopic column 16 as is evident from inspecting FIG. 3. At first, the x-ray tube casing 15 is located at a level which is about half way between its upper and lower limits of vertical travel. What will appear on the floor is shown in the inset marked 70. With a gooseneck at its zero angle position as in FIG. 1, the laser beam spot will occur at the point marked 71. A mark is made on the floor coincident with this point. The x-ray tube is then swung about the vertical axis 19 of the gooseneck to positions which are 90° apart and additional marks are made where the beam spots 72, 73 and 74 occur on the floor. Lines are then drawn between diametrically opposite beam spots 71, 73 and 72, 74. The point 75 of intersection of these lines is then marked. The same procedure is followed with the x-ray tube casing 15 at its upper travel limit and at its lower travel limit in that order or in reverse order. If the x-ray tube casing does not move perfectly vertically with the telescopic column, the point of intersection equivalent to point 75 at the various levels will not coincide but will shift. The direction of the shift or error distance between the point marked 75 and the point at which the intersection of the diametral lines is obtained at the various levels, indicates to the installer the direction in which the components of the telescopic column must be shimmed or otherwise adjusted to bring about coincidence at all levels. After adjustments are made, the test procedure is repeated. When coicidence is obtained at all levels of the tube casing, the user can be assured that the laser beam is directed perfectly vertically as will be the case with the central ray.

Anyone familar with x-ray apparatus will be aware that a telescoping vertical tube support column of the general type marked 16 is not an absolutely rigid assembly but that it flexes somewhat because of the highly offset weight of the x-ray tube casing 15 and collimator 33. The amount of flexing and resulting lateral shift is a function of the vertical elevation of the x-ray tube casing and the angular position of the gooseneck 18 which supports it. Therefore, the axis of column 16 cannot remain perfectly vertical for all vertical positions of the tube. In practice, the laser beam and column axis will be set at greatest vertical accuracy when the x-ray tube is at the middle of its vertical range. At the upper and lower limits, due to column flexing, the column axis and laser beam may be angled slightly outwardly and inwardly, respectively, with reference to the axis position at the midrange position of the tube. The described procedure was developed to allow the apparatus installer to quickly determine the best overall adjustment of the telescopic tube support column.

The next part of the procedure is called tube leveling because it has traditionally been done by placing a spirit level on a flat surface of x-ray beam collimator 33. This procedure is for assuring proper front to rear alignment of the axis 20 about which the x-ray tube casing 15 angulates in a vertical plane. Shims or whatever adjustment is available in the particular design may be required at the tube mount in order to achieve proper front to rear alignment. Misalignment will cause the x-ray beam to shift with respect to a receptor as the focal spot-to-image distance is changed and may cause cut-off of the x-ray beam by the bucky grid. X-ray examinations performed with the x-ray beam horizontal are more seriously affected by this type of misalignment. Therefore, this alignment is performed with the laser simulated central ray 35 horizontal as would be the case for the x-ray beam if the x-ray tube casing were rotated 90° about axis 20 from its solid line position over the table in FIG. 1 to make a radiograph using the wall stand cassette 32. The laser tool 21 is depicted in dashed lines where it is in its horizontal attitude.

In reality, the laser beam 35 which simulates the central x-ray will be adjusted to be horizontal and parallel with the overhead rails 22. For this test, the laser is pointed down, turned on and its beam aperture is opened. The x-ray tube is angulated to exactly 90° which is determined by observing one of the spirit levels 66 or 67 on the side of the laser housing. The x-ray tube is adjusted to a height so that its beam would be about chest high. The tube is then shifted so that the laser beam strikes the wall of the room and the laser is about six feet from the wall. The telescopic column and the carriages which support it are locked temporarily against motion. The position of the laser beam spot on the wall is marked. The x-ray tube is then moved to about three feet from the wall by pushing on the column 16 and any shift of the beam spot is recorded. Any shift should be left or right. Any vertical shift indicates that either the x-ray tube is not exactly 90° or that the overhead rails are not level. A shift of ⅛th inch or less is considered acceptable. If the shift is greater, the x-ray tube must be shimmed on its mounting or otherwise adjusted. The process is repeated and adjustments are made until drift of the beam spot on the wall is within tolerance. Finally, a flat mirror is adhered to the cassette 32 plane to determine if the laser beam is reflected back on itself as an indication of perpendicularity and the cassette holder is adjusted as required.

The table bucky 14 and cassette 13 combination may require adjustment to insure that the laser beam simulated central x-ray is perpendicular to the plane of the grid. This procedure can be performed at any time after the table is anchored to the floor. It is easiest to perform after table power has been connected and the tabletop can be driven to expose the bucky grid or the tabletop may be removed for this purpose. A flat mirror is laid on top of the bucky grid. If the grid is perpendicular to the laser beam, then the beam will reflect on itself. If a reflected beam spot is visible anywhere on the bottom end of the laser, adjustments must be made. The procedure involves positioning the x-ray tube casing with laser attached over the approximate center of the grid. The tube casing is adjusted to a height such that the bottom end of the laser is about 40 inches from the grid which is a typical focal spot-to-image distance. The small flat mirror is placed on the grid to reflect the beam. The reflected beam should land on the laser within one-half inch of the exiting beam. This tolerance will guarantee a maximum error of about 22 minutes of arc in the angle of the grid with respect to the beam. The shift tolerance applies only to a front to rear shift or grid tilt. Any tilt in the longitudinal direction is unimportant since this is merely a function of the horizontal stop position of the table which, in itself, can be easily adjusted. If the grid is tilted too far with respect to the beam, the angle of the grid should be adjusted by tilting the bucky front to back.

The adjustment means for the various parts are present in all well-designed x-ray equipment and can be assumed to be available.

So far, procedures for determining that the x-ray tube travels vertically in various orthogonal horizontal planes, that the beam is horizontal when the tube casing is rotated an intended 90° from vertical, that the beam is perpendicular to the plane of an image receptor in a table and to one mounted away from the table such as on a wall have all been demonstrated. The elementary steps for determining if the central ray is horizontal, vertical and perpendicular to various image receptor planes has been demonstrated. The techniques can be extended to verifying the level, alignment, perpendicularity or directional trueness of other relatively movable parts of the typical x-ray system which has been shown and to other more complex and differently arranged systems. In any case, horizontal and vertical movement accuracy can be determined by observing laser beam spot drift and trueness to perpendicularity may be determined by observing the beam spot reflected from the planar image receptor surface.

The method and the devices used herein have other merits. For instance, proper alignment of the laser tube 61 within its cylindrical housing 59 can be verified by simply rotating the cylinder around its longitudinal axis and observing beam spot shift. If the laser device 21 is mounted in the adapter plate 48 and rotated, the beam will appear stationary only when it is aligned to the center of the hole in the adapter plate which interfaces with the x-ray tube casing. An important aspect of the method is that it allows visualization of a laser beam which is truly coincident with an accurately determined central x-ray. The x-ray tube only has to be turned on for a brief interval for locating the bright spot on the phosphor of the locator device and then all tests can be conducted using a low energy and harmless laser beam as opposed to using an energized x-ray source as has been customary.

After all parts of the x-ray system are aligned, the laser device 21 is removed from tube casing 15 and x-ray beam collimator 33 is mounted in place of it to adapter plate 48. The system is then ready for taking radiographs.

Before the alignment devices and method described herein were developed, alignment and perpendicularity of the x-ray beam to the image receptors was determined on a preliminary basis with the use of the collimator 33 and verification was made by taking a sequence of radiographs and making suitable adjustments until the collimated x-ray beam filled the image receptor plane without overlap in any direction. Typical x-ray collimators contain a light source and a mirror system which allows projecting a light field through the collimator blade openings which is intended to simulate the x-ray field. Another light source and proper optical system produces a more focused ray which is intended to coincide with the central ray. Thus, for example, the collimator was used to try to determine if the light spot simulated central ray would follow the center line of the x-ray tabletop when the x-ray tube casing was turned on its horizontal axis where it is connected to the gooseneck. One of the problems with this is that as the collimator angulates and its beam spot and projected field intercept a tabletop surface or a planar receptor surface at a varying distance, the x-ray field edges become more diffuse and the image or field becomes enlarged and distorted and its location cannot be determined with precision. With a highly focused laser beam, however, there is no significant diffusion or spreading of the beam within the distances normally encountered in x-ray systems and much greater precision can be obtained.

Although methods for obtaining centering and perpendicularity between the central ray of an x-ray beam and image receptors at locations outside of and inside of an x-ray table have been described in detail, such description is intended to be illustrated rather than limiting, for the basic method may be variously employed and is to be limited only to the extent required by the claims which follow.

We claim:

1. A method of enabling visualization of the central ray of an x-ray beam emitted from a focal spot of an x-ray tube in a casing that has a port through which an x-ray beam may be projected and is mounted for moving relative to at least one image receptor plane in a diagnostic x-ray system, said method comprising the steps of:

installing a central ray locator device housing in an adapter which is mounted to said casing at said port and is movable transversely of the direction in which the x-ray beam is to be projected, the locator device including an element having a hole whose axis is directed at said focal spot for passing a central ray aligned with said axis, said device having a phosphor screen spaced from said hole and said screen having crosshairs on whose intersection the axis of said hole projects, energizing the x-ray tube and shifting said adapter as required until the bright spot visible on said screen due to passage of rays through said hole occurs at the intersection of said crosshairs as an indication that the central ray has been located, and then clamping said adapter to said casing, then substituting for said locator device in said adapter a housing in which there is a laser mounted in said housing such that its output beam is concident with the same axis as said hole and said crosshairs so that when said laser is energized its beam will produce a visible light spot where the invisible central x-ray would impinge.

2. The method as in claim 1 including additional steps for determining if the central ray is directed truly vertical at a time when the x-ray tube casing mounting is constrained to permit vertical movement of said casing and of the focal spot therein, said additional steps comprising:

directing said laser beam onto a substantially horizontal surface when said tube casing on its mounting is at one elevation above said surface and taking the step of marking the place where the laser light spot occurs on the surface and then repeating the step with the casing at other elevations are substantially coincident a true vertical direction of said beam is indicated and if the spots shift lack of a true vertical direction is indicated.

3. The method as in claim 1 including the additional steps for determining if the central ray is directed truly vertically in a case where the x-ray tube casing is mounted on an arm for being turned about a horizontal axis and the arm is mounted for angulating about a vertical axis on a vertically extensible and contractible column which enables the focal spot of the x-ray tube to be set at various distances from an image receptor, said additional steps comprising:

directing said laser beam onto a substantially horizontal surface when said tube casing and the focal spot therein is at one elevation above the surface and making a mark where the laser light spot occurs on the surface and then angulating the arm in 90 degree steps and making similar marks where the beam spot occurs, and then drawing lines between diametrally opposite marks to determine their point of intersection, repeating the preceding sequence of steps with the casing at least another elevation to determine another point of intersection, and then adjusting the alignment of said column until the points of intersection determined at various elevations during a repetition of said additional steps are substantially coincident.

4. The method recited in any of claims 1, 2 or 3 including the additional steps for determining if said laser beam and corresponding central x-ray are perpendicular to an image receptor plane in an x-ray table comprising:

disposing a planar reflective element in parallelism with the image receptor plane and directing the truly vertical laser beam onto said reflective element to determine if the reflected beam spot is returned along the path of the incident beam as evidenced by the beam spot being displaced from the beam output aperture of the laser if the beam and receptor plane are not perpendicular.

5. The method recited in claim 3 including the steps for performing tube leveling, said steps including:

turning said x-ray tube casing on said arm about said horizontal axis with laser device attached to an attitude wherein said laser beam will be horizontal as determined by using a spirit level and adjusting said casing relative to said support arm so said casing will repeatably latch in a horizontal attitude, projecting the horizontal laser beam onto a wall of the room while the laser is at a predetermined distance from said wall and marking the place at which the laser beam spot appears, moving said tube casing to a selected one of a greater or lesser distance from the wall while observing if the beam spot shifts to the left or right, then making any required adjustments in the angular position of said casing and laser about said vertical axis of said arm required to assure that said arm latches in a position which will result in a substantial absence of shift when the steps of projecting said beam with the casing at different distances from the wall is repeated.

6. The method as in claim 5 including the step of disposing a planar reflective element in parallelism with a vertical image receptor plane such as a wall mounted or floor stand mounted cassette, projecting the horizontally corrected laser beam onto said reflecting element to determine if the reflected beam spot is returned along the path of the incident beam as evidenced by the beam spot being displaced from the beam output aperture of the laser if the beam is not perpendicular to the image receptor plane.

* * * * *